United States Patent [19]

Gardner et al.

[11] Patent Number: 5,019,591
[45] Date of Patent: May 28, 1991

[54] METHOD FOR TREATING RETINOPATHY AND OTHER SMALL VESSEL DISORDERS ASSOCIATED WITH DIABETES

[75] Inventors: Thomas W. Gardner, Franklin; Theodore M. Hollis, State College, both of Pa.

[73] Assignee: Pennsylvania Research Corporation, University Park, Pa.

[21] Appl. No.: 312,693

[22] Filed: Feb. 17, 1989

[51] Int. Cl.$^5$ .................... A61K 31/34; A61K 31/135
[52] U.S. Cl. ..................................... 514/461; 514/648
[58] Field of Search ............................... 514/648, 461

[56] References Cited

PUBLICATIONS

Chem. Abst, 103:171798r (1985); Akihiro et al.
Dull et al. Fed. Proc. 45,462 (1986).
Hollis, Exp. Mol. Pathol., 431 90-6 (1985).
Cunha Vaz, J. G., Faria de Abreu, J. R.; Campos, A. J., Figo, G. M.; "Early Breakdown of the Blood Retinal Barrier in Diabetes," Br. J. Ophthalmol., 59, 649-56 (1975).
Waltman, S. R., Oestrich, C., Krupin, T., Hanish, S., Ratzan, S., Santiago, J.; Kilo, C., "Quantitative Vitreous Fluorophotometry, A Sensitive Technique for Measuring Early Breakdown of the Bloodretinal Barrier in Young Diabetic Patients," Diabetes, 27, 85-7 (1970).
Ishibashi, T., Tanaka, K., Taniguchi, Y., "Disruption of Blood-Retinal Barrier in Experimental Diabetic Rats: An Electron Microscopic Study,"Exp. Eye. Res, 30, 401-10 (1980).
Orlidge, A., Hollis, T. M., "Aortic Endothelial and Smooth Muscle Histamine Metabolism in Experimental Diabetes," Arteriosclerosis, 2, 142-50 (1982).
Hollis, T. M., Kern, J. A., Enea, N. A.; Cosgarea, A. J., "Changes in Plasma Histamine Concentration in the Streptozotocin Diabetic Rat," Exp. Mol. Pathol., 43, 90-6 (1985).
Hollis, T. M. Gallik, S. G., Orlidge, A., Yost, J. C.; "Aortic Endothelial and Smooth Muscle Histamine Metabolism, Relationship to Aortic 125I Albumin Accumulation in Experimental Diabetes,"Arteriosclerosis, 3; 599-606 (1983).
Ryan, T. A., Joiner, B. L., Ryan, B. F.; Minitab Student Handbook, First Edition, (1976).
Carroll, W. C., Hollis, T. M., "Retinal Histamine Synthesis is Increased in Experimental Diabetes", Invest Ophthalmol., Vis. Sci, 29, 1201-04 (1988).
Dull, R. O., Vergis, G. J., Hollis, T. M., "Effect of Chronic Histamine Infusion on the Permeability of the Blood Retinal Barrier,"Fed. Proc. 45, 462 (1986).
Katora, M. E., Hollis, T. M., "A Simple Fluorometric Method for Quantitative Determination of Aortic Protein Uptake,"J. Appl. Physiol. 39, 145-9 (1975).

Primary Examiner—Stanley J. Friedman
Assistant Examiner—Zohreh A. Fay
Attorney, Agent, or Firm—Jones, Day, Reavis & Pogue

[57] ABSTRACT

A method for treating and preventing retinopathy and for treating and preventing other small vessel complications associated with diabetes which comprises administering a therapeutically effective amount of an antihistamine or a pharmaceutically acceptable derivative thereof to a mammal having retinopathy or other small vessel complications associated with diabetes.

7 Claims, No Drawings

METHOD FOR TREATING RETINOPATHY AND OTHER SMALL VESSEL DISORDERS ASSOCIATED WITH DIABETES

BACKGROUND OF THE INVENTION

1. Field of the Invention

This invention relates to a method for treating and preventing retinopathy and other small vessel disorders associated with diabetes.

2. Description of the Prior Art

Diabetes mellitus causes retinopathy. Indeed, diabetes mellitus causes abnormal blood-ocular barrier permeability, which subsequently results in diabetic retinopathy. Nonproliferative phases of this condition are intraretinal, with primary pathogenic processes involving vascular leakage and vessel occlusion. Employing vitreous fluorophotometry, Cunha Vaz et al., Cunha Vaz, J. G., Faria de Abreu, J. R., Campos, A. J., Figo, G. M., "Early Breakdown of the Blood Retinal Barrier in Diabetes," Br. J. Ophthalmol., 59, 649–56 (1975), performed one of the earliest studies that indicated diabetic patients showed vitreal leakage of sodium fluorescein, whereas nondiabetic individuals did not. Since then, others have observed changes in blood-ocular barrier sodium fluorescein permeability in diabetic humans and rats, noting that these changes may occur before any ophthalmoscopic or angiographic signs of diabetic retinopathy are present, Waltman, S. R., Oestrich, C., Krupin, T., Hanish, S., Ratzan, S., Santiago, J., Kilo, C., "Quantitative Vitreous Fluorophotometry. A Sensitive Technique for Measuring Early Breakdown of the Bloodretinal Barrier in Young Diabetic Patients," Diabetes, 27, 85–7 (1970), Ishibashi, T., Tanaka, K., Taniguchi, Y., "Disruption of Blood-Retinal Barrier in Experimental Diabetic Rats: An Electron Microscopic Study," Exp. Eye. Res, 30, 401–10 (1980).

Causes of blood-ocular leakage in diabetics are still unresolved, although there is considerable agreement that hyperglycemia is an important contributing factor. Orlidge and Hollis, Orlidge, A., Hollis, T. M., "Aortic Endothelial and Smooth Muscle Histamine Metabolism in Experimental Diabetes," Arteriosclerosis, 2, 142–50 (1982), reported that aortic endothelial and smooth muscle cell histamine synthesis is increased in streptozotocin diabetic rats. This increase in histamine synthesis was normalized by insulin treatment, as well as by treatment with alpha hydrazinohistidine, a relatively specific inhibitor of histidine decarboxylase, Hollis, T. M., Gallik, S. G., Orlidge, A., Yost, J. C., "Aortic Endothelial and Smooth Muscle Histamine Metabolism. Relationship to Aortic 125I Albumin Accumulation in Experimental Diabetes," Arteriosclerosis, 3, 599–606 (1983), hyperglycemic rats treated with alphahydrazinohistidine also exhibited normal aortic albumin permeability characteristics in contrast to elevated permeability in diabetic rats not given this inhibitor. Plasma histamine concentrations are elevated in diabetic rats, Hollis, T. M., Kern, J. A., Enea, N. A., Cosgarea, A.J., "Changes in Plasma Histamine Concentration in the Streptozotocin Diabetic Rat," Exp. Mol. Pathol, 43, 90–6 (1985), as is retinal histamine synthesis, Carroll, W. C., Hollis, T. M., "Retinal Histamine Synthesis is Increased in the Streptozotocin Diabetic Rat, Invest Ophthalmol." Vis Sci, 29, 1201–04 (1988). Finally, chronic intravenous histamine infusion in nondiabetic rats raises their plasma histamine concentrations to those of diabetic animals, thereby increasing blood-ocular albumin leakage, Dull, R. O., Vergis, G. J., Hollis, T. M., "Effect of Chronic Histamine Infusion on the Permeability of the Blood Retinal Barrier," Fed. Proc. 45, 462 (1986).

It is further known that diabetes mellitus is responsible for other small vessel disorders in mammals. Such other small vessel complications arise in the kidney, brain (stroke), heart (heart attack), feet (peripheral vascular disease), skin (skin necrosis), and nerves (peripheral neuropathy).

It is therefore an object of the present invention to provide a method for treating and preventing retinopathy.

It is a further object of the present invention to provide a method for treating and preventing other small vessel complications which arise in connection with diabetes.

These and other objects are achieved through the application of a therapeutically effective amount of an antihistamine, or a pharmaceutically acceptable derivative thereof to a diabetic mammal which substantially prevents or minimizes the occurrence of retinopathy and other small vessel disorders which typically arise from diabetes.

SUMMARY OF THE INVENTION

This invention relates to a method for treating and preventing retinopathy and for treating and preventing other small vessel complications associated with diabetes which comprises administering a therapeutically effective amount of an antihistamine or a pharmaceutically acceptable derivative thereof to a mammal having retinopathy or other small vessel complications associated with diabetes.

DETAILED DESCRIPTION OF THE INVENTION

In accordance with one embodiment of the present invention, retinopathy and other small vessel disorders associated with diabetes mellitus are treated and prevented by a method which comprises administering to a mammal a therapeutically effective amount of an antihistamine or a pharmaceutically acceptable derivative thereof.

Antihistamines which can be employed in the process of this invention include any of the many known H-1 receptor antagonists including without limitation, diphenhydramine, terfenadine, mequitazine, astemizole, acrivastine, SCH 29851, SK&F 93944, clemastine, ketotifen, azatadine, oxatomide, azelastine, doxepine, piperoxan (933F), 929F, 1571F, mepyramine, chlorpheniramine, triprolidine, promethazine, as well as any of the many known H-2 receptor antagonists, including without limitation, burimamide, cimetidine, ranitidine, famotidine, nizatidine. Of course, any other known antihistamines, H-1 receptor antagonists and H-2 receptor antagonists may be used as well, as well as any pharmaceutically acceptable variations, derivatives, salts or preparations therefrom. Diphenhydramine and ranitidine are especially preferred antihistamines.

The antihistamines may be administered systemically in any convenient form, as well as intravenously or intramuscularly. Systemic application in pill form is preferred.

The antihistamines should be administered in a therapeutically effective amount, with dosage and regimens for the application readily ascertainable by one skilled in the art. A range of from about 1 mg/kg body mass to over 100 mg/kg body mass may be used with from about 5 mg/kg body mass to about 50 mg/kg body mass is preferred. From 2 to 24 hour intervals may be used for the application, and from 6 to 12 hour intervals is preferred.

For treating and preventing retinopathy and other small vessel disorders, the antihistamines can thus be administered orally 1 to 5 times daily at a dosage level of 100 to 10,000 mg/day, preferably, 400 to 5000 mg/day in an adult human.

Examples of the pharmaceutical preparations containing the antihistamines include tablets, capsules, powders, granules and the like. These preparations can be prepared by conventional techniques using suitable additives such as binders, colorants, excipients, disintegrators and the like.

The following examples illustrate the instant invention, but the present invention is not limited thereto.

EXAMPLES 1-5

1. Methods

A. General. Fifty male Wistar rats with initial body weights of 160-180 g were used in these examples. Diabetes was induced in 40 rats by streptozotocin injection (jugular vein, 65 mg/kg with ketamine HCl/xylazine anesthesia, 50 mg/kg and 5 mg/kg, respectively). Animals were housed individually and given standard laboratory food and water ad libitum for 28 days. Housing conditions were maintained at 25° C., 50% humidity, with a 6 a.m.-6 p.m. photoperiod. Nonfasting blood glucose determinations were made before injection and weekly afterwards. Measurements were made using a YSI glucose analyzer (Yellow Springs Instrument Co., Yellow Springs, OH). Control animals received citrated phosphate buffered saline (PBS) and were treated as above. In addition, body weights, urine glucose concentrations, urine volumes, and individual animal's fluid intakes were measured weekly.

During the last 7 days of the 28 day holding period, diabetic animals were divided into subgroups of ten animals. In Example I, one group of rats was untreated (untreated diabetic animals). Other groups of ten animals each received the following treatments; Example II—diphenhydramine-HCl (50 mg/kg at 12h, i.m.); Example III—ranitidine (5 mg/kg at 6h, i.p.); and Example IV—diphenhydramine-HCl given concurrently with ranitidine at doses and regimens listed in Examples II and III. Example V is the control group of animals.

At the end of the treatment period, animals were anesthetized as described, and fluorescein isothiocyanate conjugated to bovine serum albumin (FITCBSA, 250 mg/kg) was injected via the jugular vein. After 6 h of FITCBSA circulation, vitrectomies were performed as discussed below, and ultimately vitreal FITCBSA content was measured. Vitreal FITCBSA was determined fluorometrically as described by Katora and Hollis, Katora, M. E., Hollis, T. M., "A Simple Fluorometric Method for Quantitative Determination of Aortic Protein Uptake," *J. Appl. Physiol.* 39, 145-9 (1975), at excitation and emission wavelengths of 490 nm and 540 nm, respectively. All data were subjected to variance analysis. When justified by this analysis, differences between means were evaluated for significance using Duncan's multiple range test, Ryan, T. A., Joiner, B. L., Ryan, B. F., *Minitab Student Handbook, First Edition.* (1976).

B. Vitreous Body Preparation. Following death of the animal, the pupil was allowed to undergo postmortum dilation in order to avoid possible trauma to the iris and surrounding structures during the first steps of the vitrectomy. Aqueous humor was aspirated with a microneedle inserted through the cornea into the anterior chamber of the eye. A cruciate incision (3mm×3mm) was made in the center of the cornea, and unaspirated aqueous humor was cleared with cellulose sponges. The lens was then removed through the incision with the use of microforceps; the vitreous was removed through this same incision. Examination of the vitreous under a dissection microscope was then performed to determine if any of the retina was present on the excised vitreous. If there was such retinal contamination, the vitreous was discarded. Pooled vitreous bodies from both eyes of a single animal were weighed, homogenized with a Polytron (Brinkman Instrument Co., NY) in 10 volumes (w/v) of 0.1 mol/L sodium phosphate buffer (pH 7.4), and centrifuged for 20 min (10,000 g, 4° C.).

2. Results

Streptozotocin treated animals exhibited hyperglycemia (nonfasting plasma glucose concentrations greater than 560 mg/dl), polyuria, glycosuria, polydipsia, and decreased weight gain. Diphenhydramine and ranitidine either alone or in combination had no significant effect on any of these metabolic parameters.

The FITCBSA content of vitreous bodies from each of the treatment groups is summarized in below.

TABLE I

| Example | FITCBSA Content in mg FITCBSA $\cdot 10^{-5}$ |
|---------|-----------------------------------------------|
| I       | 5.09 ± 1.2                                    |
| II      | 3.31 ± 0.36                                   |
| III     | 2.47 ± 0.85                                   |
| IV      | 1.48 ± 0.31                                   |
| V       | 2.57 ± 0.53                                   |

These data, utilizing the methods of the instant invention, clearly indicate that the vitreous FITCBSA content of animals in the untreated diabetic group was essentially twice that of control animals. Most striking, however, is that diphenhydramine treatment of diabetic rats during the last 7 days of the holding period produced a complete reversal of vitreal FITCBSA accumulation, for the difference between this group and control animals is not significant ($p > 0.05$). In addition, ranitidine treatment also produced a complete normalization of vitreous FITCBSA accumulation, and combined drug therapy resulted in a reduction of vitreous FITCBSA content to a level significantly less than control ($p < 0.05$). These changes occurred despite the presence of hyperglycemia and all the other manifestations of diabetes.

Histamine is a known mediator of local blood flow in a variety of vascular beds, and infused histamine increases blood-brain barrier permeability. The blood-brain barrier has an embryonic origin similar to the blood-retinal barrier, Rapoport, S. I., *Blood Brain Barrier in Physiology and Medicine.* (1976). Thus, these data, utilizing the methods of the instant invention, taken in their entirety indicate that altered histamine metabolism occurs in experimental diabetes, that one manifestation is an increase in tissue and plasma histamine concentrations, and that histamine receptors are present in retinal microcirculation which can interact with this excess histamine. Indeed, it appears that one important mechanism regulating blood-ocular FITCBSA accumulation is activation of both histamine H-1 and H-2 receptors. This is supported by observations that diphenhydramine and ranitidine independently normalize vitreal FITCBSA accumulation; when given together they exert a synergistic action.

In short, data obtained utilizing the methods of the instant invention indicate activation of retinal histamine receptors is an important component of vitreal FITC-BSA accumulation in experimental diabetes.

We claim:

1. A method for treating and preventing retinopathy associated with diabetes which comprises administering a therapeutically effective amount of an antihistamine or a pharmaceutically acceptable derivative thereof to a mammal having retinopathy associated with diabetes, wherein the antihistamine is selected from the group consisting of diphenhydramine, terfenadine, mequitazine, astemizole, acrivastine, SCH 29851, SK&F 93944, clemastine, ketotifen, azatadine, oxatomide, azelastine, doxepine, piperoxan (933F), 929F, 1571F, mepyramine, chlorpheniramine, triprolidine and promethazine.

2. A method for treating and preventing retinopathy associated with diabetes which comprises administering a therapeutically effective amount of an antihistamine or a pharmaceutically acceptable derivative thereof to a mammal having retinopathy associated with diabetes, wherein the antihistamine is selected from the group consisting of burimamide, cimetidine, ranitidine, famotidine and nizatidine.

3. A method as claimed in claim 1, wherein the antihistamine is diphenhydramine.

4. A method as claimed in claim 2, wherein the antihistamine is ranitidine.

5. A method for treating and preventing retinopathy associated with diabetes which comprises administering a therapeutically effective amount of an antihistamine or a pharmaceutically acceptable derivative thereof to a mammal having retinopathy associated with diabetes, wherein the antihistamine is selected from the group consisting of diphenhydramine and ranitidine and mixtures thereof.

6. A method as claimed in claims 1, 2 or 5, wherein the therapeutically effective amount of the antihistamine is administered orally in the range of from about 5 mg/kg body mass to about 50 mg/kg body mass, from once to five times daily.

7. A method as claimed in claim 6, wherein the antihistamine or the pharmaceutically acceptable derivative thereof is administered orally in the form of tablets.

* * * * *